United States Patent
Sherik et al.

(10) Patent No.: US 11,630,054 B2
(45) Date of Patent: Apr. 18, 2023

(54) IN-SITU HIC GROWTH MONITORING PROBE

(71) Applicant: Saudi Arabian Oil Company, Dhahran (SA)

(72) Inventors: Abdelmounam Sherik, Dhahran (SA); Abderrazak Traidia, Abqaiq (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 267 days.

(21) Appl. No.: 17/108,569

(22) Filed: Dec. 1, 2020

(65) Prior Publication Data

US 2021/0102888 A1 Apr. 8, 2021

Related U.S. Application Data

(62) Division of application No. 15/879,941, filed on Jan. 25, 2018, now Pat. No. 10,866,183.

(60) Provisional application No. 62/452,464, filed on Jan. 31, 2017.

(51) Int. Cl.
| | | |
|---|---|---|
| G01N 17/04 | (2006.01) | |
| G08B 21/18 | (2006.01) | |
| G01N 7/10 | (2006.01) | |
| G01N 17/00 | (2006.01) | |
| C10G 75/00 | (2006.01) | |
| G01N 33/2025 | (2019.01) | |

(52) U.S. Cl.
CPC ............ *G01N 17/04* (2013.01); *C10G 75/00* (2013.01); *G01N 7/10* (2013.01); *G01N 17/006* (2013.01); *G08B 21/182* (2013.01); *G01N 33/2025* (2019.01)

(58) Field of Classification Search
None
See application file for complete search history.

(56) References Cited

U.S. PATENT DOCUMENTS

| | | | |
|---|---|---|---|
| 3,866,460 A * | 2/1975 | Pearce, Jr. ............... | G01N 7/10 422/112 |
| 3,996,124 A | 12/1976 | Eaton et al. | |
| 4,043,178 A | 8/1977 | Winslow, Jr. | |
| 4,056,968 A | 11/1977 | Wisnlo, Jr. | |

(Continued)

FOREIGN PATENT DOCUMENTS

WO 2008067674 A1 6/2008

OTHER PUBLICATIONS

Controlling Ultrasonic-Inspection Intervals by Monitoring Hydrogen Permeation, Peter Bo Mortensen et al., NDTnet., Oct. 1998, vol. 3, No. 10.

(Continued)

*Primary Examiner* — Lore R Jarrett

(74) *Attorney, Agent, or Firm* — Leason Ellis LLP

(57) ABSTRACT

The present application concerns in-situ intrusive probe systems and methods. The probe systems described herein can be installed flush to a hydrocarbon containing structure, such as a pipeline, vessel, or other piping system carrying crude, gas or sour products. The probe systems include hydrogen induced cracking (HIC)-resistant microstructure such that as atomic hydrogen permeates the probe surface, the probe captures recombined hydrogen gas. The pressure of the resultant hydrogen gas buildup is measured and predictions as to the HIC activity of that area can be made.

14 Claims, 7 Drawing Sheets

(56) References Cited

U.S. PATENT DOCUMENTS

| | | |
|---|---|---|
| 5,392,661 A | 2/1995 | Freeman |
| 5,405,513 A | 4/1995 | Lewis, II et al. |
| 5,495,746 A | 3/1996 | Sigwrth |
| 6,193,876 B1 | 2/2001 | Manolatos et al. |
| 6,368,954 B1 | 4/2002 | Lopatin et al. |
| 6,537,824 B1 | 3/2003 | Corea |
| 6,554,015 B1 * | 4/2003 | Witt ............ C01B 3/501 96/10 |
| 6,554,981 B2 * | 4/2003 | Lewis, II ........ G01N 27/4045 204/404 |
| 6,814,854 B2 | 11/2004 | Lewis, II et al. |
| 6,984,857 B2 | 1/2006 | Udayakumar et al. |
| 2004/0112857 A1 | 6/2004 | Herschbein et al. |
| 2005/0012126 A1 | 1/2005 | Udayakumar et al. |
| 2008/0148862 A1 | 6/2008 | Aikens |
| 2010/0089584 A1 | 4/2010 | Burns |
| 2011/0139321 A1 | 6/2011 | Murakami et al. |
| 2012/0090380 A1 * | 4/2012 | Wetzig ............ G01N 15/00 73/31.04 |
| 2014/0161553 A1 | 6/2014 | Carl |
| 2015/0300989 A1 | 10/2015 | Masleid et al. |
| 2015/0301010 A1 | 10/2015 | Valentini |
| 2016/0379723 A1 | 12/2016 | Martynov et al. |

OTHER PUBLICATIONS

Traidia et al.. "An effective finite element mode for the prediction of hydrogen induced cracking in steel pipelines", IHE, 16214-16230, Sep. 10, 2012.

Bob Winters, "Cleaning Pig designs and applications", Apr. 17, 2014 (Apr. 17, 2014), pp. 1-24, XP05547159, Slides 7, 8 and 20.

\* cited by examiner

IN-SITU HIC GROWTH MONITORING PROBE

CROSS-REFERENCE TO RELATED PATENT APPLICATIONS

This application is a divisional of U.S. patent application Ser. No. 15/879,941, filed Jan. 25, 2018, which is based on and claims priority to U.S. Provisional Patent Application 62/452,464, filed Jan. 31, 2017, the entire contents of which are incorporated by reference herein as if expressly set forth in their respective entireties herein.

FIELD OF THE INVENTION

The present invention generally relates to assessing asset damage to metal structures. More particularly, the present invention relates to probe systems for assessment of hydrogen-induced damage to metal pipelines.

BACKGROUND OF THE INVENTION

Hydrogen-induced cracking (HIC) is a persistent problem for metal (e.g., steel) structures, such as pipelines, pressure vessels, and other piping systems, and particularly those that are composed of non-HIC resistant steel and service hydrocarbon products (e.g., sour gas or natural gas). Naturally occurring acid gases in hydrocarbon products, such as $CO_2$ and $H_2S$, dissolve in the water phase of the hydrocarbon liquid product. The electrochemical reactions associated with these processes yield atomic hydrogen, which is adsorbed onto the corroding internal wall surfaces of the asset. The majority of this adsorbed atomic hydrogen recombines onto the steel surfaces, forming molecular hydrogen (hydrogen gas), and "bubbles off" with no damage to the steel. However, in the presence of $H_2S$, a certain portion of the adsorbed atomic hydrogen does not recombine into hydrogen gas, but instead permeates through the steel surface, diffuses through the metallic lattice and eventually recombines inside "voids" within the metal wall thickness. These voids are associated with metallurgical defects formed during the steel making process (typically Manganese sulfide (MnS) non-metallic inclusions). The pressure resulting from the hydrogen gas generated inside these voids can reach very high values (up to 12,000 bars, i.e., 1,200 MPa in the absence of passivation of the steel surfaces). These very high pressures contribute to the local reduction in cohesive forces at the tip of non-metallic inclusions (hydrogen embrittlement), and ultimately lead to blisters, crack initiation and subsequent growth of HIC. HIC cracks can also lead to the more critical through-thickness cracking termed Step-Wise Cracking (SWC). Blisters and cracks associated with HIC and SWC can grow over time and result in the failure of a metal pipeline.

Integrity engineers manage HIC-induced degradation and maintain structure integrity by performing regular inspection of pipelines to identify and monitor HIC-affected areas. For example, integrity engineers perform In-Line Inspection (ILI) of pipelines to identify HIC clusters that are thereafter excavated for closer inspection by Advanced Ultrasonic Testing (AUT). AUT is conducted to validate ILI results, determine the remaining wall thickness of the pipeline, and also to check for the presence of SWC (which cannot be detected using conventional ILI techniques, such as magnetic flux leakage and conventional ultrasonic testing). These results are then analyzed using industry standard codes for fitness-for-service (FFS)—(such as API-579 or ASME B31G) and an integrity decision is made. AUT examinations are carried out on high severity locations to obtain the data required for the assessment. Based on the outcome of the assessment, AUT examinations are carried out more frequently with the frequency in part typically depending upon inspection for linear HIC or step-wise cracking (SWC). However, this approach is not feasible for pipelines due to the impracticality and cost-ineffectiveness of conducting frequent AUT examinations (e.g., semi-annually) for buried transmission pipelines and to the difficulty of prioritizing of multiple affected line sections on the same line. Furthermore, AUT examinations lack a way to identify and prioritize inspection of highly active HIC active areas that may emerge in between inspections.

Moreover, conventional in-situ systems practice electrochemical methods, pressure-based methods, and vacuum-based probe methods that calculate corrosion rates indirectly from measured permeating gas rates and thus are non-intrusive to the pipeline. Non-intrusive electrochemical methods and probes, as well as pressure-based and vacuum-based probes, have limited sensitivity for measuring hydrogen as they can only measure hydrogen buildup that passes from the structure's internal surface to the structure's external surface. Most hydrogen that diffuses from the inside wall of a structure does not diffuse completely through the structure to its external surface, but rather the hydrogen is entrapped inside the wall thickness. This limitation underestimates the amount of hydrogen generated and the actual pressure can be much higher and therefore can lead to miscalculated corrosion rates since the corrosion rates are based on the measurement of hydrogen buildup. Further, such probes are not practical for buried lines and can include measurement chemicals that are impracticable for intrusive field application in regard to chemical liquids in present in assets.

As such, there exists a need to provide warning systems that identifies hydrogen pressure buildup active areas and to prioritize AUT examinations to inspect the most HIC active areas of a metal structure first. There further exists a need for an intrusive in-situ monitoring probes. It is in regard to these issues and others that the present invention is provided.

SUMMARY OF THE INVENTION

Throughout the specification, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. Similarly, the phrase "one or more embodiments" as used herein does not necessarily refer to the same embodiment and the phrase "at least one embodiment" as used herein does not necessarily refer to a different embodiment. The intention is, for example, that claimed subject matter includes combinations of example embodiments in whole or in part.

The present disclosure details intrusive warning probe systems and methods for installation at an oil or gas structure surface (e.g., a steel pipeline) in order to monitor and measure hydrogen pressure buildup. To install the probe system, a hole is bored through the pipeline surface and a coupling mount having a threaded inner surface is seated in the hole. The probe system is then screwed into the coupling mount via an access fitting. Specifically, probe installation is arranged such that an exposed surface of the probe is positioned at least substantially flush to the inner surface of the structure (i.e., "flush geometry"). The exposed probe surface is made of the same material grade as the structure surface to ensure that the same corrosion and hydrogen induced cracking (HIC) processes take place at both the probe and the oil/gas structure, though unlike the structure surface, the exposed probe surface is metallurgically modified to have HIC-resistant microstructure. In this way, diffusing hydrogen can enter the probe system, but will not become trapped in metallurgical cavities inside the exposed probe surface.

The probe system includes a HIC-simulation cavity (collection cavity or internal cavity) in which diffusing atomic hydrogen (H) permeates to and recombines within the cavity to form hydrogen gas ($H_2$). To ensure that all permeating atomic hydrogen remains in the cavity and does not escape back into the oil/gas structure, one or more surfaces of the cavity include atomic hydrogen diffusion barrier. As hydrogen gas content in the cavity increases, the pressure in the cavity increases correspondingly, mimicking the HIC process. The system monitors the cavity pressure with a hydrogen sensor (e.g., digital hydrogen gauge, transducer, etc.) and determines corresponding hydrogen build-up rates. High hydrogen build-up rates indicate an increased chance of HIC or step-wise cracking (SWC), thereby providing a warning system as to which structure areas likely need engineer inspection. Additionally, the simulation cavity is advantageously designed to have a significantly smaller volume than commercially available probes, which provides higher monitoring sensitivity to pressure build-ups.

In one aspect, provided herein are probe systems that comprise a probe body that has an access end and a base end. At the access end, an exposed surface is exposed to a corrodent. At the base end is a cap threaded to interlockingly engage with the base end of the probe body. In one or more embodiments, the probe body has a solid first end portion defined by the exposed surface configured to be exposed to the corrodent located within the metal asset. The probe body has an internal opening that terminates at a location spaced from the exposed surface. An insert, such as a filler rod, is disposed within the internal opening (blind hole) of the probe so as to define a collection cavity defined between the insert and an inner wall of the probe body. In one or more embodiments, a diffusion barrier is disposed along the inner wall of the probe body and is formed of a material that is at substantially impermeable to a gas generated in the collection cavity by the corrodent so as to prevent passage of the gas from the collection cavity to the surrounding inner wall of the probe body. A conduit is in fluid communication with the collection cavity for receiving the gas generated by the corrodent. In one or more embodiments, a pressure measuring device is coupled to the conduit for measuring a pressure of the gas created by the corrodent. For example, the pressure measuring device can be a pressure gauge or transducer.

In another aspect, provided herein are probe systems that comprise a probe body that has an access end and a base end. At the access end, an exposed surface is exposed to a corrodent. At the base end is a cap threaded to interlockingly engage with the base end of the probe body. In one or more embodiments, the probe has a probe body including an access end portion with an exposed surface configured to be exposed to a corrodent located within the metal asset. The access end portion has a recessed portion formed opposite the exposed surface. An insert has an access end and a base end, with the access end being disposed adjacent recessed portion of the probe body so as to define a collection cavity that is fluid-tight and configured to collect the corrodent that permeates through the exposed surface of the probe body, whereby a gas is generated in the collection cavity by the corrodent. The insert includes a through hole that passes therethrough and is open at both the access end and the base end such that the through hole is in fluid communication with the collection cavity.

In one or more embodiments, a pressure measuring device is coupled to the conduit for measuring a pressure of the gas created by the corrodent. For example, the pressure measuring device can be a pressure gauge or transducer.

Provided herein are methods for warning for hydrogen induced cracking (HIC). The method includes inserting an intrusive probe system into a metal structure that is at least substantially flush to the inner wall of the metal structure. The intrusive probe system is as described herein. Next, atomic hydrogen is allowed to permeate the exposed surface of the probe system. Thereafter, molecular hydrogen is generated in the internal cavity of the probe system. The pressure of the molecular hydrogen is then measured. The method then determines whether the measured pressure identifies a risk of hydrogen induced cracking. Finally, the method schedules advanced ultrasonic testing according to the risk of hydrogen induced cracking.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF THE INVENTION

Figure 1A:
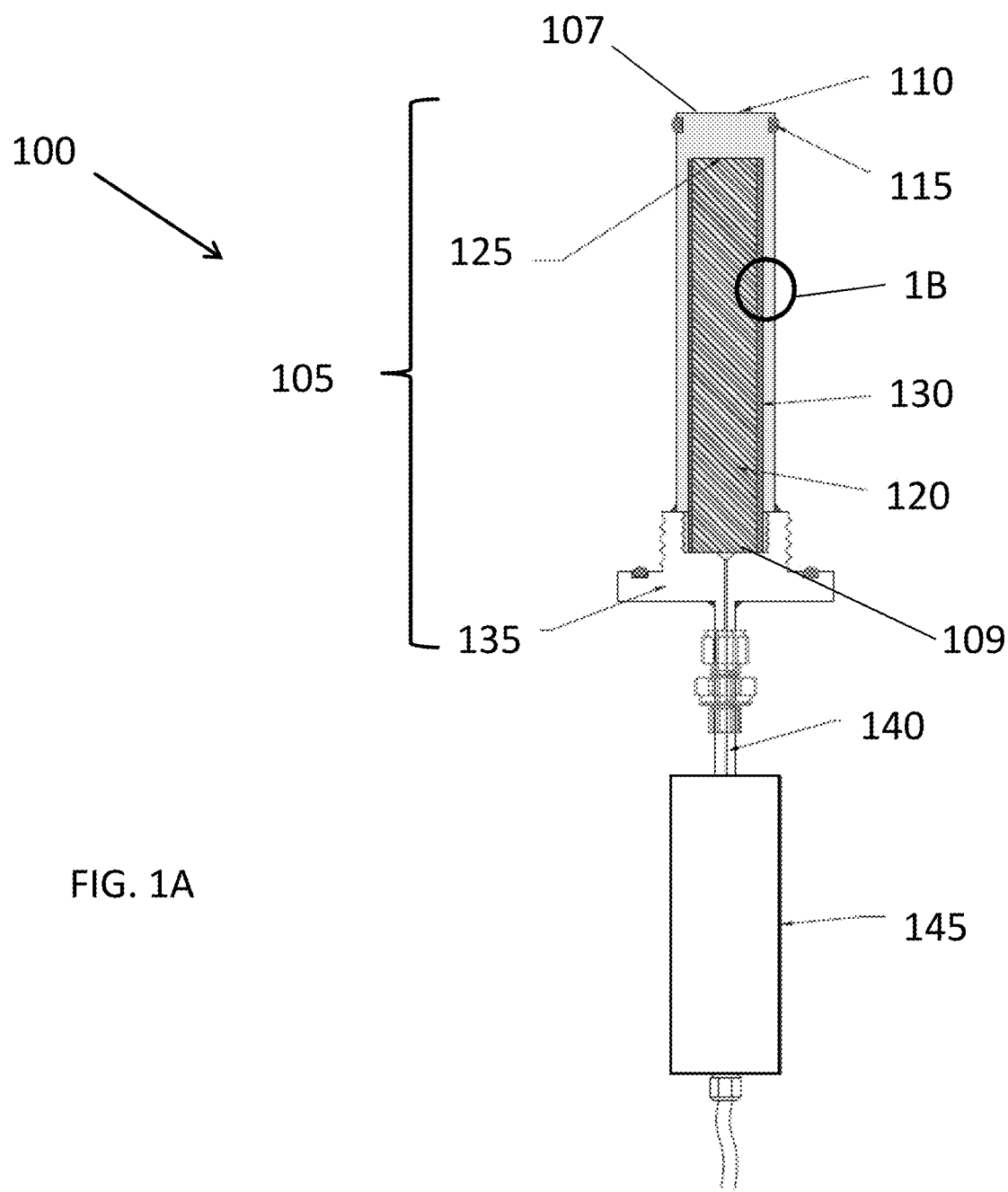
FIG. 1A illustrates an intrusive probe system according to one or more embodiments of the present invention.

As described herein, a "structure" can include oil or gas pipelines, other containers, or metal assets. For example, the probe systems described herein can be implemented at a steel pipeline structure.

Provided herein are in-situ intrusive probe systems and methods that mimic voids associated with HIC cracks in steel structures, such as pipelines, pressure vessels, and piping systems. The intrusive probe systems simulate hydrogen pressure build-up occurring from the recombination of atomic hydrogen generated from corrosion processes caused by transported hydrocarbon products (crude, gas, or sour disposable waters) in pre-existing HIC cracks detected during Advanced Ultrasonic Testing (AUT) or In-Line Inspection (ILI) inspections. Specifically, the probe systems described herein couple to the outer surface of the structure and provide a probe hydrogen entry surface that is at least substantially flush with the internal surface of the structure. An at least substantially flush geometry ensures that the exposed entry surface of the probe is liquid tight to the internal wall of the structure such that the probe experiences the same fluid flow characteristics (e.g., fluid velocity, shear stress, local water content and chemistry) as the rest of the structure internal wall, and further, the flush geometry ensures that internal inspection procedures and/or cleaning procedures are not impeded.

The in-situ, or "at the site," measuring and monitoring of hydrogen pressure build up as performed by the intrusive probe systems and methods described herein includes the following steps in one or more embodiments: (1) reviewing existing ILI maps for the structure (e.g., an oil or gas pipeline) of interest, and identifying locations of HIC clusters or locations of maximum corrosion rates; (2) boring an access point in the structure wall within the vicinity of these identified locations; (3) mounting a coupling mount at the access point; (4) threading the probe system through an access fitting and screwing the access fitting to the coupling mount until the probe surface is flush with in the internal surface of the structure; (5) monitoring of the hydrogen pressure build up at the probe system with a pressure sensing device (e.g., digital hydrogen gauge, transducer, etc.) as atomic hydrogen permeates the probe system and recombines to hydrogen within a cavity in the probe; and (6) performing AUT examinations at the most HIC active areas on priority basis (i.e., areas that show highest hydrogen pressure build rates). AUT examinations can be prioritized because measured hydrogen pressure data is correlated with HIC growth rate as established from first principles equations or determined from experimental work and/or extensive field experience (i.e., empirical correlation between pressure build-up rate and HIC growth rate determined from successive ILI runs). The hydrogen pressure data is collected via real-time online monitoring or off-line monitoring, such as with a data logger. In one or more embodiments, the probe systems described herein include a wireless communication system as is known in the art to communicate between the probe system and a remote control area.

In this way, the intrusive probe systems and methods described herein optimize inspection resources by optimizing and prioritizing excavation digs and AUT inspections, monitor process upsets, provide a mechanism for studying the effect of added chemicals (e.g., DRA, inhibitors) on hydrogen permeation through steel. Further, the data collected can be used to build more accurate HIC/SWC prediction models.

With reference now to FIG. 1, an intrusive probe system 100 according to one or more embodiments is provided. The probe 100 includes a probe body 105 having an access end 107 and a base end 109 that is configured to be positioned such that the access end 107 is flush to a metal structure (e.g., structure 205 of FIG. 2A) and exposed to the liquids or gas in which atomic hydrogen is produced. As shown in the FIG. 1, probe body 105 can be formed so as to have an opening (bore) formed therein so as to define an internal cavity, with the access end 107 being the closed end of the probe body 105, while the base end 109 is an open end in which the opening in the probe body 105 is accessible.

The access end 107 of the probe body 105 includes an exposed (outer) surface 110. The exposed surface 110 is made of the same metal (e.g., steel) grade as the structure to be monitored, but has a HIC-resistant microstructure. This arrangement permits atomic hydrogen to pass into the probe 100, as described below, to form hydrogen gas by the same mechanism and same rates as in the surrounding structure, but the HIC-resistant microstructure of the access end 107 prevents hydrogen gas from becoming entrapped in metallurgical cavities. In other words, in the closed end (access end 107), there is no formation of molecular hydrogen and instead the atomic hydrogen is free to pass through this material to a cavity (which mimics voids associated with HIC cracks) as described below. It will be appreciated that molecular hydrogen still forms along the exposed surface of the access end 107 and bubbles off, but the permeating portion of hydrogen does not get entrapped inside the body the access end 107 due to the access end 107 being made of a HIC-resistant steel which has no metallurgical defects that entrap hydrogen. Further, the HIC-resistant microstructure (of the probe body 105) militates against the development of HIC/SWC cracks within the probe system 100 itself. In one or more embodiments, the access end 107 of the probe 100 includes one or more O-rings 115. The O-rings 115 are arranged about the outer surface of the probe body 105 adjacent to the access end 107 to ensure liquid-tight geometry such that no liquid enters between the probe and structure wall.

Figure 1B:
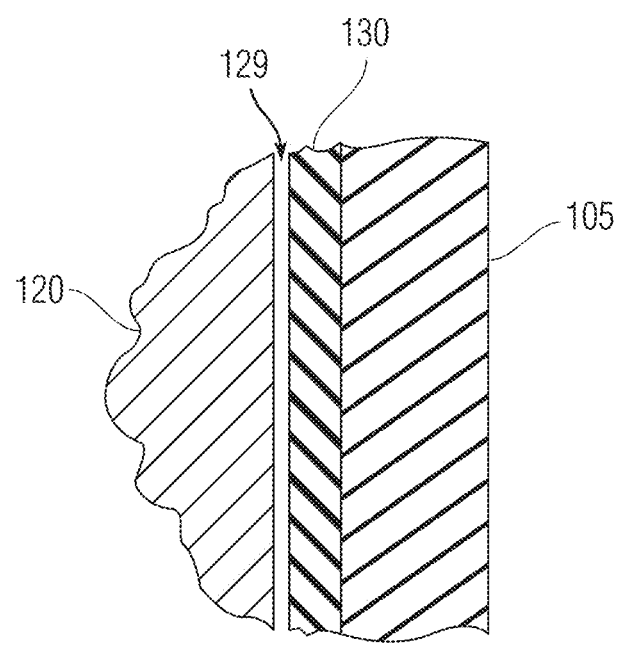
FIG. 1B is a greatly magnified view of a portion of the intrusive probe system of FIG. 1 showing an internal cavity that can have a width of between about 10 microns and 50 microns in one embodiment.

As mentioned above, the probe body 105 includes an internal cavity 129 (hollow space) (See, FIG. 1B) to collect diffused hydrogen gas that has passes through the access end 107 of the probe 100. The internal cavity 129 is defined, at least in part, by the closed ended opening, formed in the body 105 and in one or more embodiments, the internal cavity 129 is also defined by a filler rod (an insert) 120 that is inserted into the opening formed in the probe body 105. In other words, the internal cavity 129 is formed between the filler rod 120 and the inner wall of the hollow probe body 105 as best shown in FIG. 1B. The filler rod 120 has a first (access) end and a second or (base end) end is inserted in the internal cavity, thereby creating and defining the internal cavity 129 that receives the atomic hydrogen from the access (closed) end 107. It will be appreciated that the cavity 129 is the result of the tight fit of the filler rod into the bore. The tight fit will leave an annuli (the space of the annuli will be determined by surface roughness of the filler rod 120 and the surface roughness of the inner wall of the hollow probe body 105. It will be appreciated that width of the annuli space (cavity 129) can be approximately 10 microns to 50 microns. However, it will be appreciated that these values are not limiting and it is within the scope of the present invention that dimensions outside of this range can equally be possible. The internal cavity 129 terminates in an internal end wall 125 that is proximate but spaced from the exposed surface 110 as shown in FIG. 1A.

In the exemplary embodiment as shown in FIG. 1, the filler rod 120 extends longitudinally from the base end of the probe body 105 toward the access end 107. The first end of the filler rod 120 is thus identified as the end nearer to the access end 107 of the probe body 105, and the second end of the filler rod 120 is identified as the end nearer to the base end 109 of the probe body 105.

The first end of the filler rod 120 can be placed into abutting relationship (i.e., in intimate contact) with the access end 107 of the probe body 105, thereby defining the internal cavity 129 (for hydrogen collection) as being between an outer surface of the side wall of the filler rod 120 and the inner wall of the probe body 105 that defines the opening formed in the probe body 105. In the embodiment in which the filler rod 120 has a cylindrical shape and the opening in the probe body 105 has a circular shape, the internal cavity 129 has an annular (ring) shape. One end of the annular shaped cavity 129 abuts the access end 107 of the probe body 105 and therefore the atomic hydrogen that passes through the access end 107 enters into the annular shaped cavity 129 at this end. As described below, the filler rod 120 is formed of a material that is not conductive to hydrogen diffusivity and therefore, the atomic hydrogen cannot migrate into the filler rod 120 from the access end 107 of the probe body 105. Instead, the atomic hydrogen is channeled into the annular shaped cavity that surrounds the filler rod 120. The first end of the filler rod 120 can be joined to the access end 107 (i.e., the end wall defining the opening formed in the probe body 105) using any number of conventional techniques.

It will be appreciated that the size of the opening (bore) formed in the probe body 105 and the size of the filler rod 120 determines the size of the internal cavity 129 that receives the atomic hydrogen. Careful control over these parts allows one to create an internal space (annular shaped cavity) that provides increased sensitivity of the probe 100 for measuring hydrogen gas buildup within the probe 100. Atomic hydrogen present in the oil or gas structure diffuses through the exposed surface 110 to the annular shaped internal cavity 129 where it can recombine to form hydrogen gas (molecular hydrogen).

As mentioned above, in one or more embodiments, the filler rod 120 is made of materials having low or no hydrogen diffusivity. For example, the filler rod 120 can be made of austenitic stainless steel or oxidized carbon steel or glass. The selection of this type of material for filler rod 120 forces the atomic hydrogen that passes through the access end 107 of the probe 100 to be directed to the annular shaped cavity surrounding the filler rod 120 as opposed to passing into and through the filler rod 120 itself.

In one or more embodiments, the material between the end of the filler rod 120 and the exposed surface 110 can be made of the same metallic grade and have the same HIC-resistant microstructure as the exposed surface. In other words, the access end 107 (i.e. the closed end of the body 105) is formed of the same material that defines the exposed surface 110 since exposed surface 110 in effect is an outer surface of the access end 107.

In one or more embodiments, a diffusion barrier 130 is provided and located within the annular shaped cavity to prevent hydrogen gas captured by the probe body 105 (i.e., hydrogen gas located within the annular shaped cavity) from escaping to the surrounding environment (i.e., to the pipeline or external environment). More particularly, the diffusion barrier 130 can be formed along the inner side wall of the probe body 105 that defines the opening formed therein and therefore, the annular shaped (hydrogen collection) cavity is formed between the side wall of the filler rod 120 and the diffusion barrier 130 (See, FIG. 1B). Since, as mentioned above, the filler rod 120 is formed of a material that has low or no hydrogen diffusivity and therefore, in combination with the diffusion barrier 130, define a collection cavity in which both the inner and outer walls that define the collection cavity 129 are designed to prevent the escape of hydrogen therethrough.

The diffusion barrier 130 can be formed of any number of suitable materials so long as they prevent hydrogen diffusion and for example, can be an oxide layer (e.g., iron oxide) or other coating (e.g., austenitic stainless steel layer, and a ceramic layer, such as $Si_3N_4$) that is formed along the cavity wall (i.e., outer cavity wall) by heat-treating the cavity in an oxygen-rich atmosphere. In this way, the amount of captured hydrogen can be reliably measured without atomic hydrogen or the hydrogen gas diffusing into the surrounding structure (e.g., as by diffusing into the side wall of the body 105 that surrounds the diffusion barrier 130).

With continued reference to FIG. 1, a cap 135 is coupled to the base end 109 of the probe body 105. In one or more embodiments, the cap 135 is threaded to interlockingly engage with the base end 109 of the probe body 105. In other embodiments, the cap 135 is coupled to the probe body 105 by other means, such as screws, adhesives, fasteners, or the like. The cap 135 can be made of any suitable materials, such as metal or plastic. An O-ring 137 can be provided to ensure a sealed fit between the cap 135 and an adjacent, abutting structure as described below. As shown in the figures, the collection cavity 129 is at least partially defined by the cap 135 since one end of the filler rod 120 is disposed within the cap 129 and the collection cavity 129 is formed about the filler rod 120.

A conduit 140 is further coupled to the base end of the filler rod 120. The conduit 140 can be a channel, pipe or tube that is designed to capture the hydrogen gas combined within the annular shaped cavity (collection cavity or chamber) (it will also be understood that some atomic hydrogen may combine in the conduit 140 to form hydrogen gas). The conduit 140 is further coupled to a pressure measuring device 145. The conduit 140 is in fluid communication with the annular shaped cavity 129 such that the hydrogen gas in the annular shaped cavity 129 flows into the conduit 140 and then as the hydrogen gas passes through the conduit 140, the pressure measuring device 145 measures the pressure caused by hydrogen build-up, which in turn provides an estimate of the hydrogen buildup in-situ at the structure (e.g., pipe wall). The hydrogen gas will thus flow along the annular shaped cavity 129 and underneath the bottom end of the filler rod 120 to access the conduit 140. The pressure measuring device 145 can be a pressure gauge or transducer or other suitable device.

Figure 2A:
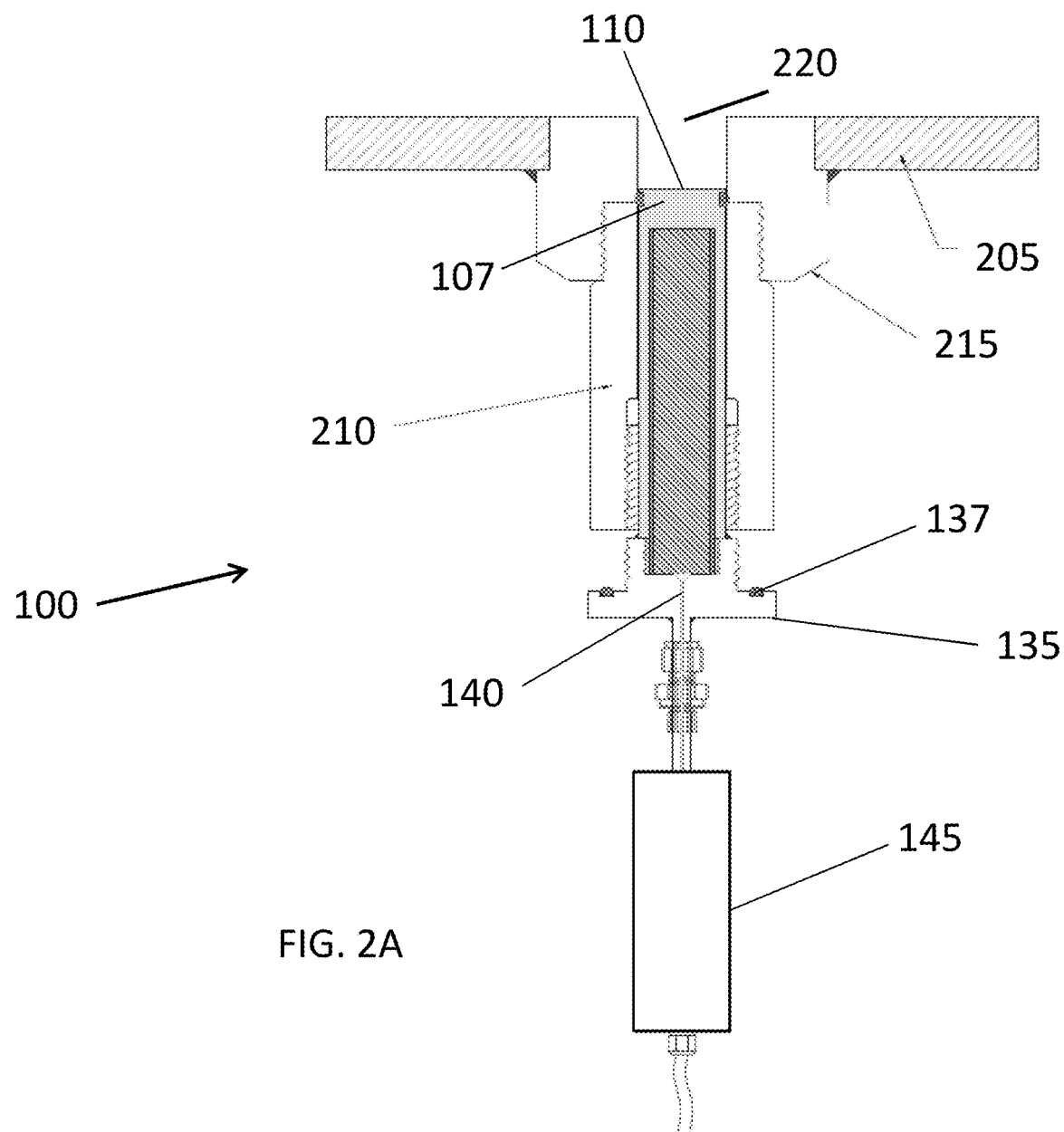
FIG. 2A illustrates the intrusive probe system of FIG. 1 as mounted into an oil or gas structure.
Figure 2B:
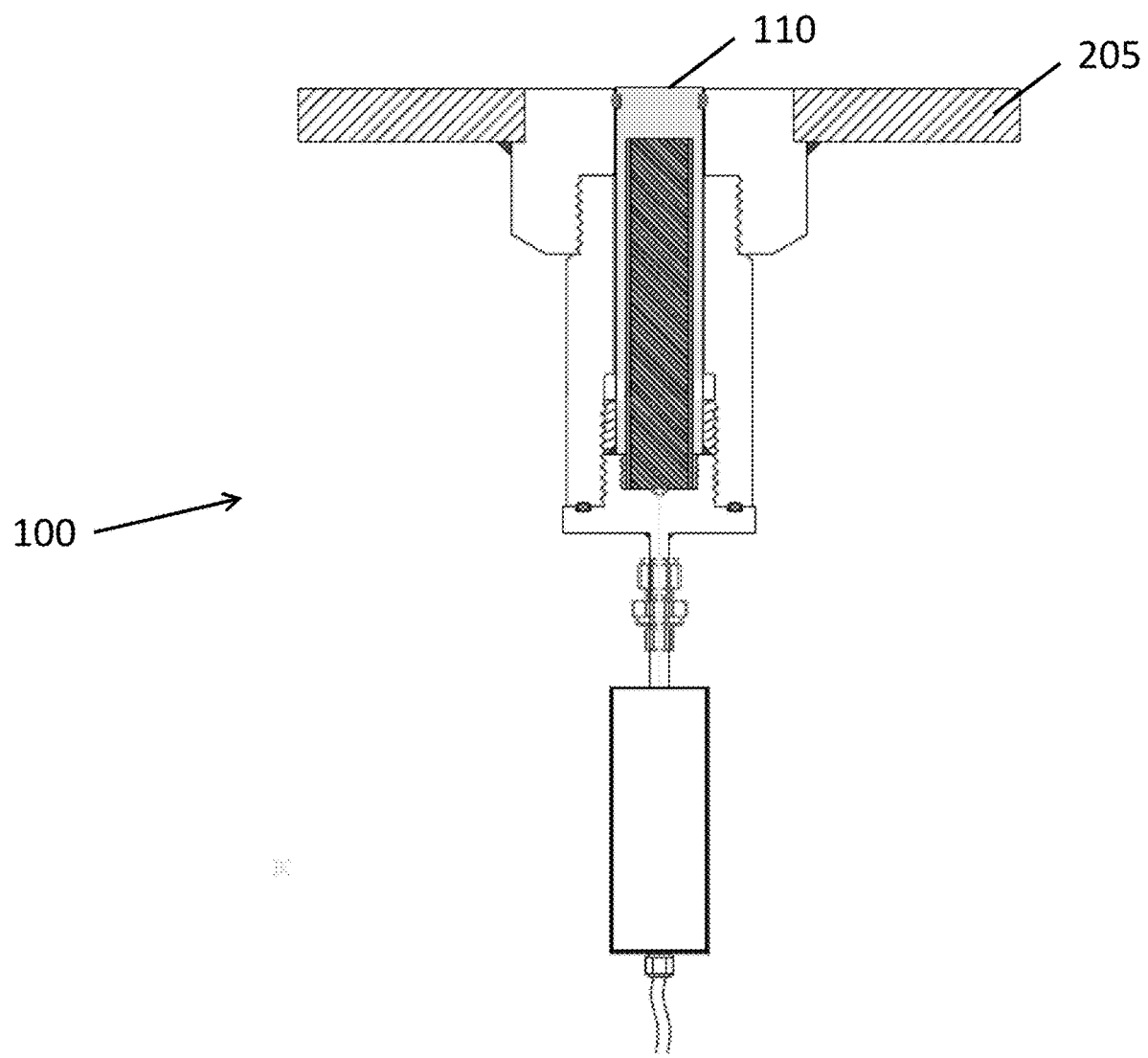
FIG. 2B illustrates the intrusive probe system of FIG. 1 as mounted into an oil or gas structure and configured to be flush to the inner surface of the structure.

With reference now to FIGS. 2A-B, the installation of probe system 100 to a structure 205 is illustrated. The structure 205 can be a metal (e.g., steel) structure that transports hydrocarbon products, such as a pipeline, pressure vessel, or other piping system transporting oil or gas. To couple the probe system 100 to the structure 205, the probe system is first coupled to an access fitting 210. In one or more embodiments, the access fitting 210 is a threaded metal or plastic component that is sized and shaped to couple with the cap 135 or other portion of probe body 105. In other embodiments, the access fitting 210 is coupled to the probe body by screws, adhesives, fasteners, or the like. The access fitting 210 and the cap 135 couple to form an air-tight seal to prevent any hydrogen gas from escaping. A hole is bored through the wall of structure 205 that is sized and shaped to receive the probe system 100. In certain embodiments, a coupling mount 215 is secured at the hole bored in structure 205 in order to receive the access fitting 210. For example, the coupling mount 215 can be a threaded metal or plastic component that is sized and shaped to mate with the access fitting 210.

As shown in FIG. 2A, the probe system 100 is secured within the access fitting 210, the access fitting being coupled to the coupling mount 215 such that an entry mouth 220 to the structure 205 is the same or similar size as the exposed surface 110 of the probe system. Then, as shown in FIG. 2B, the probe system 100 is coupled in place such that the exposed surface 110 is flush to the inner wall of structure 205. The probe system 100 is considered to be "flush" if it is installed such that the exposed surface 110 does not extend substantially beyond the inner wall of the structure 205 and is not recessed relative to the inner wall of the structure 205 (e.g., it is less than about 1 mm from the inner wall of the structure 205. The probe system 100 is not considered to be flush if it is merely installed on the outer wall of the structure 205, as in a "patch probe." Unlike patch probes, in which atomic hydrogen recombines in the structure wall before ever reaching the patch probe, in the flush configuration, the probe system 100 captures diffused atomic hydrogen at the boundary of the structure 205, which recombines to molecular hydrogen in the cavity of the probe instead of in the structure itself. This arrangement better mimics HIC generation and allows for increased and more accurate hydrogen flux measurement than with patch probes. Additionally, the flush arrangement of probe system 100 provides advantages over fully intrusive probe types (i.e., in which the probe extends into the structure beyond the inner wall, typically into the hydrocarbon product—for example, the Model 6400 hydrogen probe manufactured by Rohrback Cosasco), as in those types water accumulates in a space between the probe and the structure surface, which changes the local pH around the probe and affects corrosion rates and hydrogen permeation rates. Thus, with fully intrusive probes, the measured pressure build up does not reflect true hydrogen entry to the probe at the structure section. Moreover, the flush geometry of probe system 100 does not impede pipeline operations (e.g., cleaning and inspection operations), and does not allow liquid or gas to escape the structure 205.

Figure 3:
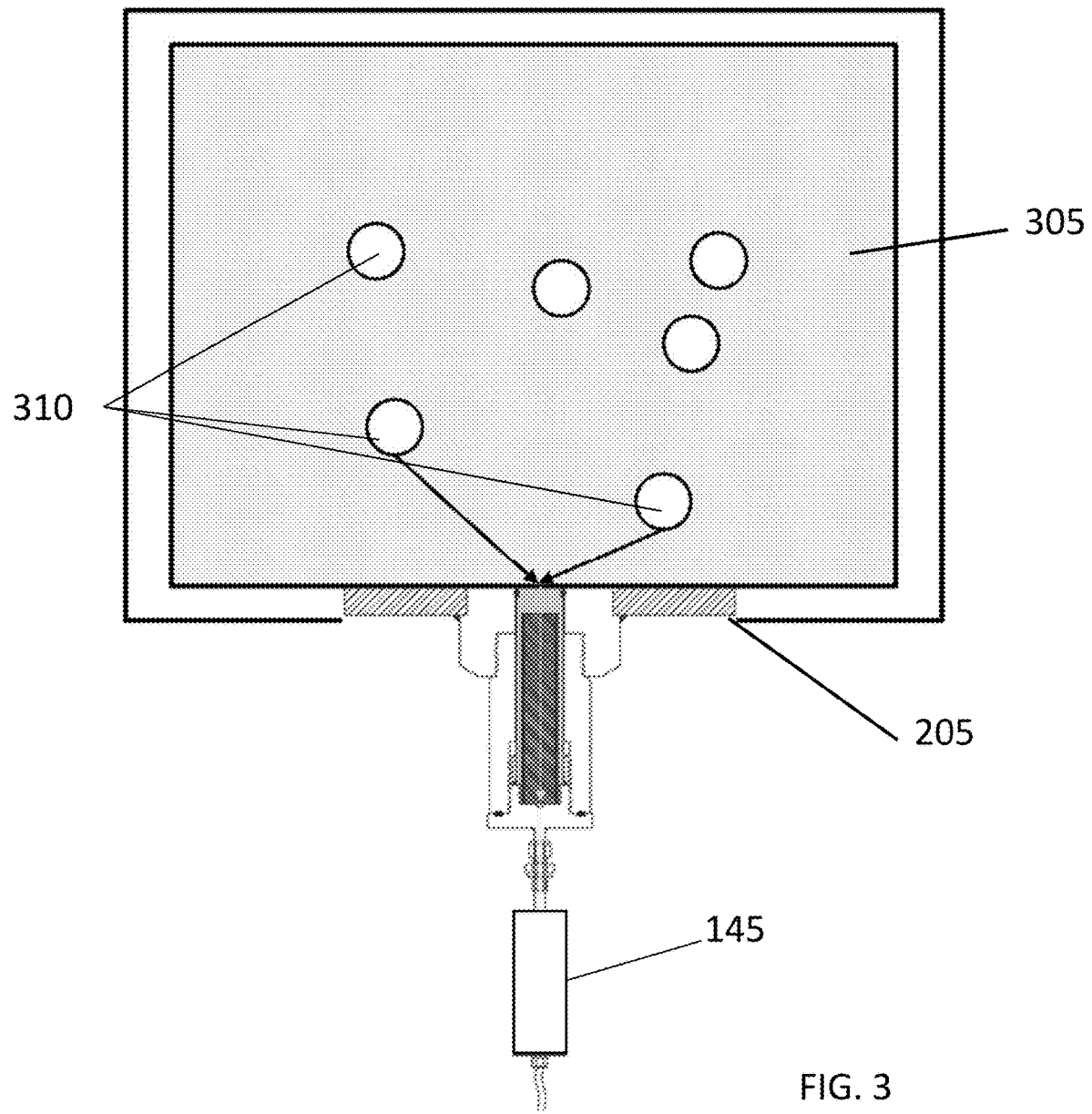
FIG. 3 illustrates the generation of atomic hydrogen and recombination of hydrogen gas within a cavity of an intrusive probe system according to one or more embodiments of the present invention.

With reference now to FIG. 3, the generation of atomic hydrogen and recombination of hydrogen gas within a cavity of an intrusive probe system according to one or more embodiments of the present invention is illustrated. For example, the probe system 100 could be installed at least substantially flush to structure 205 as previously described. The structure 205 contains liquid or gas hydrocarbon products 305 in liquid or gas form that produce atomic hydrogen 310. Atomic hydrogen 310 migrates to the inner surface of structure 205, where it permeates the surface of the structure 205 and recombines into hydrogen gas. As shown in FIG. 3, certain atomic hydrogen 310 permeates the exposed surface 110 of the probe system 100 which, as mentioned, is installed in a flush orientation. As previously discussed, after passing through the access end 107 of the probe body 105, the atomic hydrogen flows into the hydrogen collection cavity 129, described above, where it combines into hydrogen gas. The hydrogen gas continues to the conduit 140, where it is collected and the pressure is measured by pressure measuring device 140.

Figure 4:
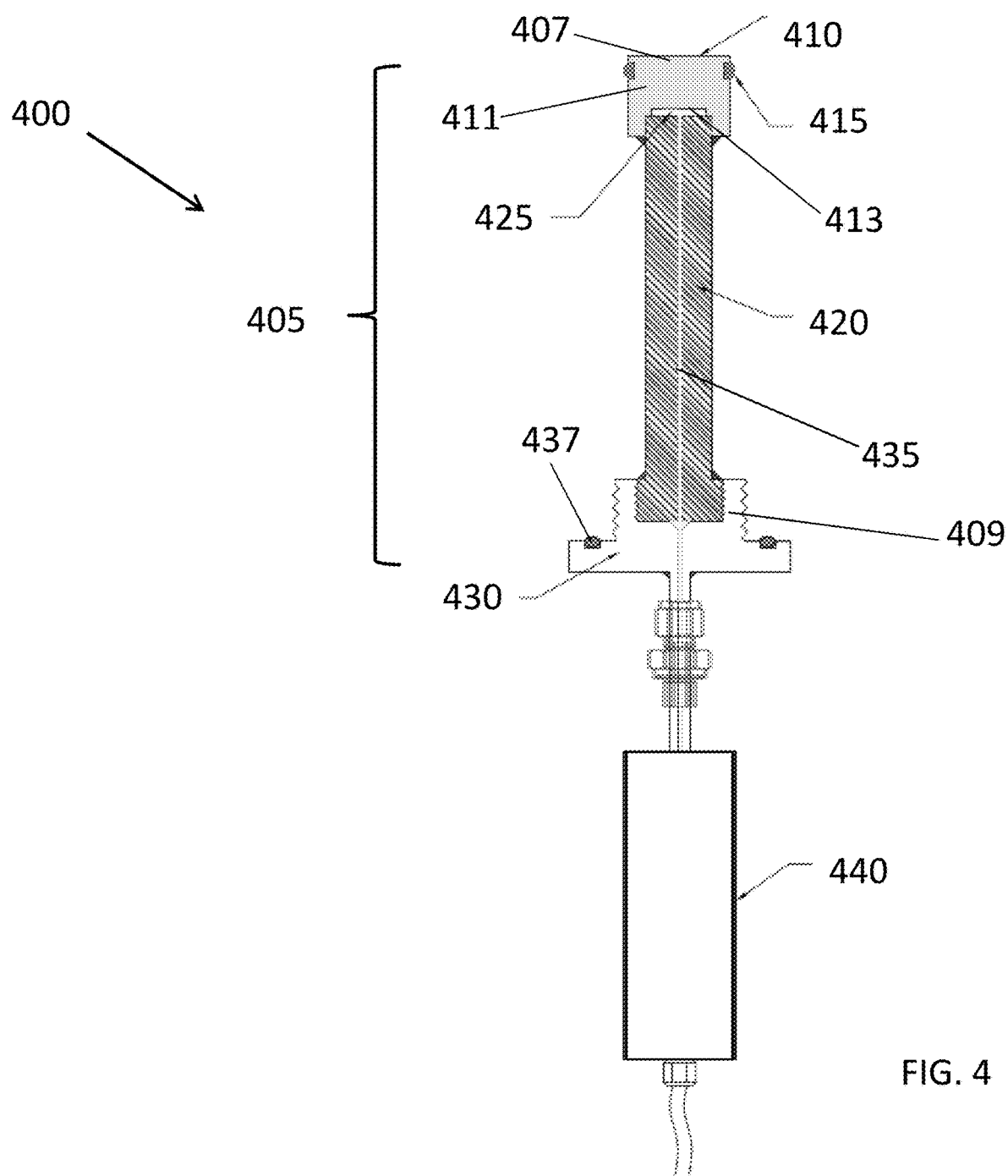
FIG. 4 illustrates an alternative intrusive probe system according to one or more embodiments of the present invention.

With reference now to FIG. 4, an alternative intrusive probe system 400 according to one or more embodiments of the present invention is provided. Probe system 400 includes a probe body 405 having an access end 407 and a base end 409, the probe system 400 being configured to be positioned such that the access end 407 is flush to a metal structure (e.g., a pipeline) and exposed to the liquids or gas in which atomic hydrogen is produced. In this way, probe system 400 is configured to have the same flush geometry as probe system 100. The access end 407 of the probe body 405 includes an exposed surface 410. Like exposed surface 110, the exposed surface 410 is made of the same metal (e.g., steel) grade as the structure to be monitored, but has a HIC-resistant microstructure. In one or more embodiments, the access end 407 of the probe 400 includes one or more O-rings 415. The O-ring(s) 415 is arranged about the outer surface of the probe body 405 to ensure liquid-tight geometry such that no liquid enters between the probe and structure wall when the probe system 400 is installed.

In the illustrated embedment, the probe body 405 is formed of multiple parts that are coupled together to form the assembled probe body 405. More specifically, the probe body 405 includes an access end member 411 and a filler rod 420 that is received within the access end member 411. The access end member 411 includes the exposed surface 410 along one face thereof and a face opposite the exposed surface 410 includes a recessed portion 413 in which a first end (access end) of the filler rod 420 is received. The recessed portion 413 formed in the access end member 411 not only receives the first end of the filler rod 420 but also serves to define a hydrogen collection cavity 425 defined between the first end of the filler rod 420 and a floor of the hydrogen collection cavity 425. As shown, the recessed portion 413 can have a stepped construction in which a landing defined therein provides a surface to which the first end of the filler rod 420 seats against. The access end member 411 has a width greater than the filler rod 420 since the filler rod 420 is received internally therein.

The first end of the filler rod 420 is coupled to the access end member 411 using any number of conventional techniques, including the use of fasteners, bonding agents, adhesives, etc. In the illustrated embodiment, the first end of the filler rod 420 is coupled to the access end member 411 by means of a weld as shown.

The filler rod 420 has a second end (base end) that is coupled to a cap 430 (e.g., the same or similar to cap 135). An O-ring 437 can be provided on the cap 430 to ensure a sealed fit between the cap 430 and another abutting structure. In one or more embodiments, the filler rod 420 is a metal rod having low or no hydrogen diffusivity. For example, the filler rod 420 can be made of an austenitic stainless steel or other materials disclosed herein.

As illustrated and unlike probe system 100, the filler rod 420 of probe system 400 is not inserted into an opening formed in the probe body for collecting recombined hydrogen gas but instead is inserted into the recessed portion of the access end member 411.

Instead, in one or more embodiments, the hydrogen collection cavity 425 is an adjustable cavity 425 that mimics the creation of HIC voids. More specifically, the size (volume) of the cavity 425 can be tailored to different particular applications. The adjustability is at a manufacturing level in that the dimensions of the recessed portion can be selected. In particular, the recessed cavity 425 can be formed at a greater depth to create a cavity of increased volume, while the recessed cavity 425 can be formed at a lesser depth to create a cavity of reduced volume. In addition, the location of the landing that receives the first end of the filler rod 420 can be varied so as to alter the volume of the cavity 425. The volume of the adjustable cavity 425 can thus be changed to simulate HIC arising at different thickness depths of the structure. As the volume of the adjustable cavity 425 is reduced, the probe system 400 sensitivity to pressure build-ups increases. In certain embodiments, the volume of the adjustable cavity 425 is 2-3 cm$^3$, 1-2 cm$^3$ or 0.0314 cm$^3$ to 0.628 cm$^3$ (with higher sensitivity being obtained with the smaller cavity size). It will also be appreciated that for smaller sized cavities, the higher the observed pressure rates and as a result, the user will have to release the entrapped hydrogen gas in the annulus at a greater frequency. In other words, higher sensitivity results in more frequent probe re-initialization.

In certain embodiments, the depth of the adjustable cavity 425 from the exposed surface 410 is less than 1 cm. In certain embodiments, the depth of the adjustable cavity 425 from the exposed surface 410 is less than about 0.5 cm.

As atomic hydrogen permeates the exposed surface 410, it passes through the access end member 411 into the adjustable cavity 425 where it recombines into hydrogen gas in the adjustable cavity 425.

A conduit 435 is formed in the filler rod 420 and more particularly, the conduit 435 can be a longitudinal channel that extends along the length of the filler rod 420 and is open at both the first and second ends of the filler rod 420. The conduit 435 is also in fluid communication with the adjustable cavity 425 as well as passing through the cap 430 so as to also be in fluid communication with a pressure measuring device 440. In other words, the conduit 435 can be thought of as a continuous channel that passes through the probe body 405, cap 430 and at least a portion of the pressure measuring device 440. Like conduit 140, hydrogen gas builds up in the adjustable cavity 425 and then passes to the pressure measuring device 440 by flowing through the conduit 435. The pressure measuring device 440 can be any hydrogen pressure gauge or transducer.

As with the previous embodiment, the access end member 411 is formed of a material that is HIC resistant but permits passage (diffusion) of the atomic hydrogen to the hydrogen collection cavity 425 for recombination therein. In contrast, the filler rod 420, like filler rod 120, has low or no hydrogen diffusivity properties and therefor, the hydrogen gas formed in the cavity 425 flows into the conduit 435 formed in the filler rod 420 and does not diffuse into the filler rod 420 itself. As a result, the formed hydrogen gas passes through probe 400 to the pressure measuring device 440 which is configured to measure the hydrogen gas buildup as a result of atomic hydrogen permeation without significant loss to the surrounding structure.

Figure 5:
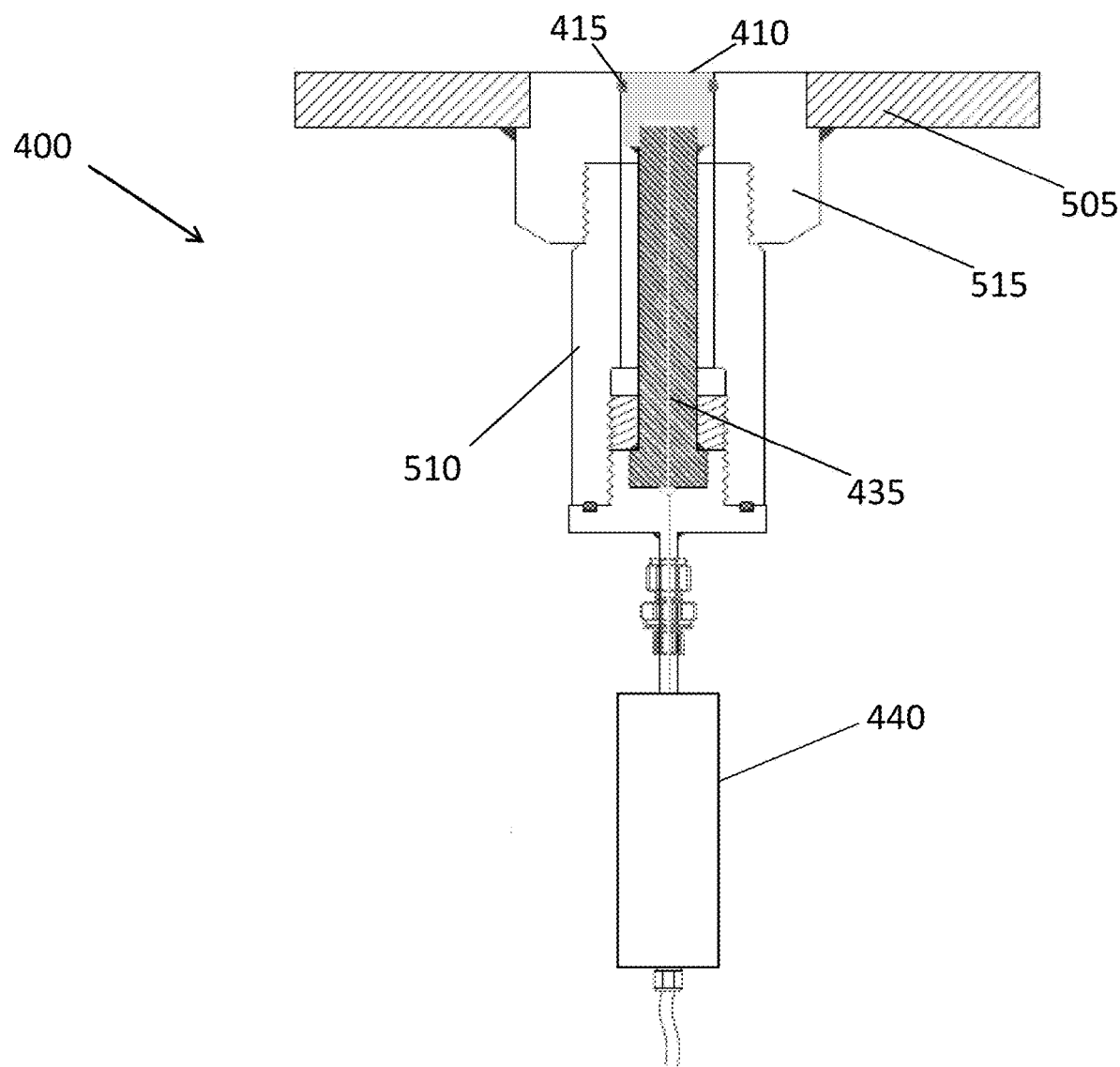
FIG. 5 illustrates the alternative intrusive probe system of FIG. 4 as mounted into an oil or gas structure and configured to be flush to the inner surface of the structure.

With reference now to FIG. 5, the installation of probe system 400 to a structure 505 is illustrated. The structure 505 can be a steel structure that transports hydrocarbon products, such as a pipeline, pressure vessel, or other piping system transporting oil or gas. As in other embodiments, the probe system 400 is coupled to an access fitting 510, which in turn is coupled to a coupling mount 515. As shown in FIG. 5, the access end member 411 of the probe system 400 is installed flush to the inner wall of the coupling mount 515 and the exposed surface 410 is installed at least substantially flush to the inner surface of the structure 505. In this arrangement, no hydrocarbon product within the structure 505 can pass into the probe body 405 without passing through the exposed surface 410. An O-ring 415 is also preferably provided to form a liquid and gas tight seal between the probe 400 (i.e., the access end member 411 thereof) and the coupling mount 515.

In the illustrated embodiment, the access fitting 510 can be an open ended structure that has a central opening that receives the probe body. As shown, at least a portion of the central opening of the access fitting 510 can be threaded (inner threads) and the cap 430 includes outer threads that mate with the inner threads to couple the probe 400 to the access fitting 510. It will also be appreciated that the threaded arrangement allow adjustment of the probe 400 relative to the access fitting 510 and in particular, the length of the probe 400 that extends beyond the distal end of the access fitting 510 can, in at least one embodiment, be changed by the threaded arrangement between the two parts. In another embodiment, there is a fixed position (orientation) between the probe 400 and the access fitting 510.

The probe systems as described herein can be implemented to provide a warning system as to possible HIC damage in sections of a structure. If the hydrogen pressure increases beyond certain thresholds, that indicates that an inspection (e.g., AUT) should be performed. Additionally, if the probe system indicates that a particular section has increased chances of HIC or SWC cracking, then nearby sections of the structure may also be scheduled for inspection.

As such, provided herein are methods for warning for hydrogen induced cracking. In this method, an intrusive probe system, such as probe system 100 or probe system 400, is installed at a structure (e.g., steel pipeline, pressure vessel, piping system). Installation may be performed as described herein, such as by implementing coupling components such as cap 135, access fitting 210 and coupling mount 215. Next, atomic hydrogen is produced by natural hydrocarbon processes within the structure. The atomic hydrogen permeates the structure and an exposed surface of the probe system (e.g., exposed surface 110, exposed surface 410). The atomic hydrogen migrates to a cavity, where it recombines to form hydrogen gas. The cavity can be filled with a filler rod, or the cavity can be adjustable, as in adjustable cavity 425. The method continues in that the pressure of the molecular hydrogen in the cavity is measured. Such measurements can be made by a pressure gauge, transducer, or other suitable hydrogen pressure device. If the pressure is higher than a particular threshold, a risk of HIC or SWC is present. The method then determines whether the measured pressure presents such a risk. There are multiple methods for making such determination. For example, a first method uses first principle calculations (See, Traidia et al., IJHE 2012, which is incorporated by reference in its entirety. A second method uses an empirical correlation (developed in laboratory experiments) between pressure increase rate and measured crack growth rate (AUT).

If a risk of HIC or SWC is identified, the method can then alert the user and schedules an AUT inspection at that area of the structure. Scheduling can be done automatically, such as by including a communication device at the pressure device that transmits a signal to a processor upon measuring a particular pressure that the processor processes using suitable software to schedule an inspection.

In one embodiment, a device (PIG) that is used to carry out ILI inspection can pick up the measurements wirelessly from the probes (e.g., using Zigbee technology or related technology) while traveling inside the pipeline. As is known in the industry, PIGs are devices that are in-line-inspection (ILI) tools used to detect the conditions of the pipeline, such as detecting and measuring corrosion. The measurements from the probe can then be integrated directly into the ILI report and help interpret the results and make decision on whether or not to go for dig verification and/or repair. The probe of the present invention can thus include a communication module (e.g., wireless module or other communication protocol (e.g., Bluetooth) that communicates with a module in the PIG to enable data transfer and communication therebetween. Communication between the PIG and the probe allows for data collection by the PIG as it moves along the inner surface of the pipeline and therefore a single report can be generated from the collected data.

The probe construction of the present invention was tested in a number of experiments that monitored hydrogen pressure build-up in the collection cavity of a period of time under conditions that simulated a void in a pipeline that carries a fluid that induced sour corrosion on the exposed surface. The results were that hydrogen pressure build-up was observed in the simulated void over a period of days, thereby indicating that the probe construction of the present invention is effective at monitoring and detecting conditions within the pipeline that are indicative of HIC or SWC formation and growth in the pipeline.

FIGS. 1 through 5 are conceptual illustrations allowing for an explanation of the present invention. Those of skill in the art should understand that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps).

In software embodiments, computer software (e.g., programs or other instructions) and/or data is stored on a machine-readable medium as part of a computer program product, and is loaded into a computer system or other device or machine via a removable storage drive, hard drive, or communications interface. Computer programs (also called computer control logic or computer readable program code) are stored in a main and/or secondary memory, and implemented by one or more processors (controllers, or the like) to cause the one or more processors to perform the functions of the invention as described herein. In this document, the terms "machine readable medium," "computer program medium" and "computer usable medium" are used to generally refer to media such as a random access memory (RAM); a read only memory (ROM); a removable storage unit (e.g., a magnetic or optical disc, flash memory device, or the like); a hard disk; or the like.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. An intrusive probe system for flush insertion into a metal asset comprising:
a probe body having an access end member that is formed as a single solid body with an exposed surface configured to be exposed to a corrodent located within the metal asset, the access end member having a recessed portion formed opposite the exposed surface, the recessed portion being defined by a first wall that is parallel to the exposed surface;
an insert having an access end and a base end, the access end of the insert being disposed within the recessed portion such that the access end member surrounds and is directly coupled to the insert and is in contact with the access end of the insert, the access end of the insert being parallel to and spaced from the first wall of the recessed portion of the probe body so as to define a collection cavity that is fluid-tight and configured to collect the atomic hydrogen that permeates through the exposed surface of the access end member, wherein the insert includes a conduit that passes therethrough and is open at both the access end and the base end such that the conduit is in fluid communication with the collection cavity; and
a pressure measuring device in fluid communication with the conduit of the insert for measuring a pressure of the gas generated by the diffused atomic hydrogen within the collection cavity.

2. The probe system of claim 1, wherein the recessed portion is formed along a face of the access end portion opposite the exposed surface.

3. The probe system of claim 1, wherein the recessed portion has a stepped construction including a landing portion against which the access end of the insert sealingly seats.

4. The probe system of claim 1, wherein the through hole is centrally located within the insert.

5. The probe system of claim 1, wherein the access end portion has a cylindrical shape.

6. The probe system of claim 1, further including a probe cap that is coupled to the base end of the insert, the probe cap having a through hole that axially aligns with the through hole formed in the insert to define a conduit to the pressure measuring device.

7. The probe system of claim 1, wherein the insert comprises a cylindrical shaped filler rod.

8. The probe system of claim 1, further including an O-ring coupled to the access end portion adjacent to the exposed surface.

9. The probe system of claim 1, wherein the access end portion is formed of a material that permits diffusion of atomic hydrogen therethrough but has an HIC resistant microstructure.

10. The probe system of claim 1, wherein the insert is formed of an austenitic stainless steel material.

11. The probe system of claim 1, further including a probe cap that is coupled to the base end of the insert; an access fitting to which the probe body is coupled;
and a coupling mount that is configured to be sealingly inserted into an access hole formed in the metal asset and to which the access fitting is coupled.

12. The probe system of claim 1, wherein the pressure measuring device is configured to send an alert once the hydrogen build-up rate reaches a threshold value that is indicative of an increased chance of HIC or step-wise cracking (SWC) in the metal asset.

13. An intrusive metal probe system for flush insertion into a metal asset comprising:
an access end member that is formed as a single solid body with an exposed surface configured to be exposed to a corrodent located within the metal asset, the access end member having a recessed portion formed opposite the exposed surface and being defined by a first wall that is parallel to the exposed surface;
an insert being at least partially disposed within the recessed portion of the access end member such that the access end member surrounds and is directly coupled to the insert and is in direct contact with the access end of the insert, the access end of the insert being parallel to and spaced from the first wall of the recessed portion of the access end member, the insert having a base end opposite the access end, the access end of the insert being disposed within the access end member so as to define a collection cavity that is fluid-tight and configured to collect the atomic hydrogen that permeates through the exposed surface of the access end member, the collection cavity being formed between the access end of the insert and the first wall of the recessed portion of the access end member, wherein the insert includes a conduit that passes therethrough and is open at both the access end and the base end such that the conduit is in fluid communication with the collection cavity;
a cap, the base end of the insert being received within a recessed portion formed in the cap such that the cap is in contact with and surrounds the base end of the insert; and
a pressure measuring device in fluid communication with the conduit of the insert for measuring a pressure of the gas generated by the diffused atomic hydrogen within the collection cavity.

14. The probe system of claim 13, wherein the conduit is formed centrally within the insert.

\* \* \* \* \*